United States Patent [19]

Fliri et al.

[11] Patent Number: 4,855,421
[45] Date of Patent: Aug. 8, 1989

[54] 2-OXOAZETIDINES, METHODS FOR THEIR PREPARATION, AND THEIR USE

[75] Inventors: Hans Fliri; Ching Pong Mak, both of Vienna, Austria

[73] Assignee: Sanraku Incorporation, Tokyo, Japan

[21] Appl. No.: 180,200

[22] Filed: Apr. 20, 1988

Related U.S. Application Data

[63] Continuation of Ser. No. 852,947, Feb. 25, 1986, abandoned.

[30] Foreign Application Priority Data

Jul. 13, 1984 [DE] Fed. Rep. of Germany ....... 3425847
Aug. 22, 1984 [DE] Fed. Rep. of Germany ....... 3430853

[51] Int. Cl.$^4$ .................. C07D 205/08; C07D 403/04
[52] U.S. Cl. .................................... 540/357; 540/359; 540/360; 540/361
[58] Field of Search ............... 540/200, 357, 359, 360, 540/361

[56] References Cited

U.S. PATENT DOCUMENTS

3,959,267  5/1976  Naylor ................................ 540/360
4,485,110 11/1984  Osborne .............................. 540/360
4,595,532  6/1986  Miller ................................ 540/360

FOREIGN PATENT DOCUMENTS

1409804 10/1975 United Kingdom ................ 540/360

OTHER PUBLICATIONS

"Protective Groups in Organic Chemistry" (McOmie) pp. 204–207.
"Protective Groups in Organic Chemistry" (Greene) pp. 172–177 and 193–203.
"Hackh's Chemical Dictionary", 5th Edition, pp. 53, 80, 440–442.
Hardi, Chem Abs. 96, 181026p (1982) Index Entry for 6 RN 81520-34-5.

Primary Examiner—Mark L. Berch
Attorney, Agent, or Firm—Robbins & Laramie

[57] ABSTRACT

The invention relates to new 2-oxoazetidines having the formulas

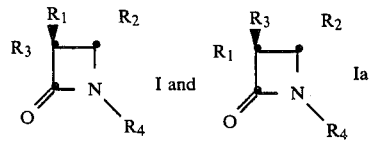

where $R_1$ stands for a lower fluoroalkyl or an optionally protected lower hydroxyalkyl group; $R_2$ for chlorine, bromine, iodine, fluorine, an

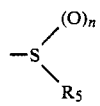

group in which n is 0, 1 or 2 and $R_5$ is a lower alkyl, lower alkenyl, an optionally substituted benzyl group, optionally substituted phenyl group, a —CH$_2$COX group in which X means a lower alkyl, lower alkoxy or the amino group, or a

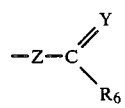

group in which Y and Z are the same or different and in each case stand for oxygen, nitrogen or sulphur and $R_6$ stands for a lower alkyl, lower alkoxy, lower alkylthio, lower dialkylamino, an aryl, aryloxy or arylthio group, or for a group having the formula

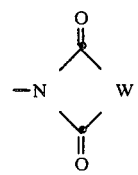

II where W stands for —CH$_2$CH$_2$—, —CH=CH— or C$_6$H$_4$; $R_3$ stands for bromine, chlorine, iodine, SeC$_6$H$_5$ or SC$_6$H$_5$; and $R_4$ stands for hydrogen, a group having the formula

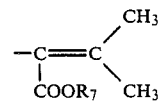

IIa in which $R_7$ is a lower alkyl, an optionally substituted benzyl or an optionally substituted benzohydryl group; or they represent a protecting group, with the proviso that in compounds of formula Ia $R_2$ does not stand for SCH$_3$ when $R_1$ means hydroxyethyl, $R_3$ means bromine and $R_4$ means the group of formula IIa, as well as to methods for their preparation and to their use.

5 Claims, No Drawings

2-OXOAZETIDINES, METHODS FOR THEIR PREPARATION, AND THEIR USE

This application is a continuation of application Ser. No. 06/852,947, filed Feb. 25, 1986, now abandoned.

The invention relates to new 2-oxazetidines having the formulas

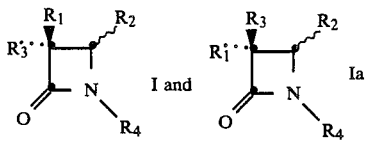

I and Ia where $R_1$ stands for a lower fluoroalkyl group or an optionally protected lower hydroxyalkyl group; $R_2$ stands for chlorine, bromine, iodine, fluorine, an

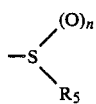

group in which n is 0, 1 or 2 and $R_5$ is a lower alkyl, lower alkenyl, an optionally substituted benzyl group, an optionally substituted phenyl group, a —$CH_2COX$ group in which X means a lower alkyl lower alkoxy or the amino group, or a

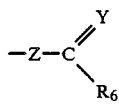

group in which Y and Z are the same or different and in each case stand for oxygen, nitrogen or sulphur and $R_6$ stands for a lower alkyl, lower alkoxy, lower alkylthio, lower dialkylamino, an aryl, aryloxy or arylthio group, or for a group having the formula

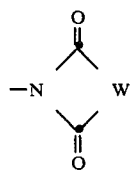

II where W stands for —$CH_2CH_2$—, —CH=CH— or $C_6H_4$; $R_3$ stands for bromine, chlorine, iodine, $SeC_6H_5$ or $SC_6H_5$; and $R_4$ stands for hydrogen, a group having the formula

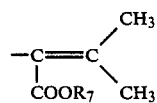

IIa in which $R_7$ is a lower alkyl, an optionally substituted benzyl or an optionally substituted benzhydryl group; or they represent a protecting group, with the proviso that in compounds of formula Ia $R_2$ does not stand for $SCH_3$ when $R_1$ means hydroxyethyl, $R_3$ means bromine and $R_4$ means the group of formula IIa, as well as to methods for their preparation and to their use.

The compounds having formula I are obtained in accordance with the invention in the following manner:

(a) To prepare compounds of formula

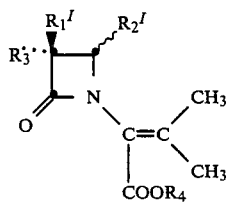

Ib where $R_3$ and $R_7$ have the meaning given above, $R_1^I$ stands for an optionally protected lower hydroxyalkyl group and $R_2^I$ for an

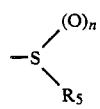

group in which n and $R_5$ have the meaning given above, a compound having the formula

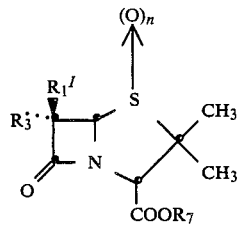

III where n, $R_1^I$, $R_3$ and $R_7$ have the meaning given above is reacted in the presence of a base with an electrophilic compound having the formula

A—$R_5$   IV where A means a leaving group and $R_5$ has the meaning given above, or with a Michael acceptor, or (b) to prepare compounds of formula

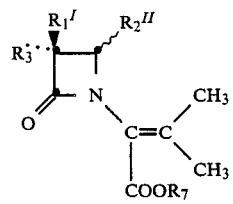

Ic where $R_1^I$, $R_3$ and $R_7$ have the meaning given above and $R_2^{II}$ stands for chlorine, bromine, iodine or —O-COCH$_3$, a compound having the formula

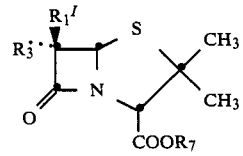

IIIa in which $R_1^I$, $R_3$ and $R_7$ have the meaning given above is halogenated or reacted with mercury(II)acetate, or (c) to prepare compounds of formulas

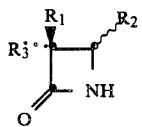  Id or

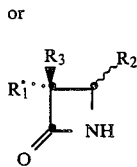  Ie where $R_1$, $R_2$ and $R_3$ have the meaning given above, from compounds having the formula

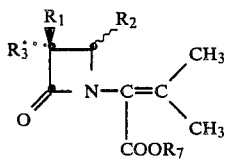  If or

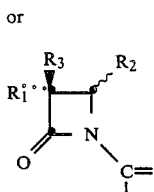  Ig where $R_1$, $R_2$, $R_3$ and $R_7$ have the meaning given above, group IIa is split off using methods known per se, or (d) to prepare compounds of formulas

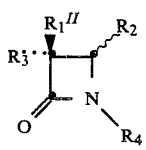  Ih or

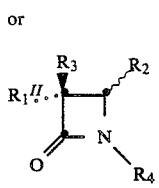  Ii where $R_2$, $R_3$ and $R_4$ have the meaning given above and $R_1^{II}$ stands for a lower fluoroalkyl group, fluorine is substituted for the optionally protected hydroxy group in a compound having the formula

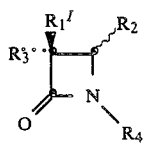  Ij or

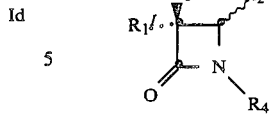  Ik or (e) to prepare compounds of formulas

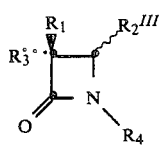  Il or

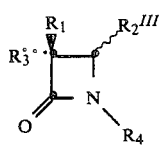  Im where $R_1$, $R_3$ and $R_4$ have the meaning given above and $R_2^{III}$ has the same meaning as $R_2$ with the exception of halogen, a compound having the formula

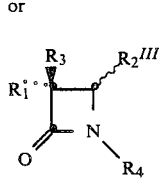  In or

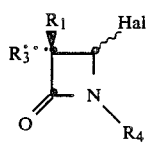  Io where $R_1$, $R_3$ and $R_4$ have the meaning given above and Hal stands for chlorine, bromine or iodine, is reacted with an ammonium salt, an alkali metal salt or an alkaline earth metal salt $M\text{-}R_2^{III}$, or (f) to prepare compounds of formulas

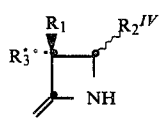  Ip or

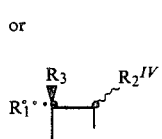  Iq where $R_1$ and $R_3$ have the meaning given above and $R_2^{IV}1$ stands for

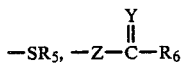

or a group of formula II, a compound of formula

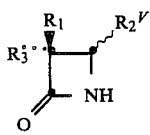

or

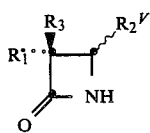

where $R_1$ and $R_3$ have the meaning given above and $R_2^V$ stands for chlorine, bromine, iodine, acetoxy or $-SO_2-R_5$, is reacted with an alkali metal salt, an alkaline earth metal salt or ammonium salt of formulas

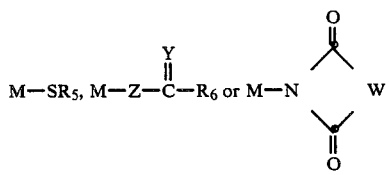

where M stands for the said cations and $R_5$, $R_6$, W, Z and Y have the meaning given above, or (g) to prepare compounds of formulas

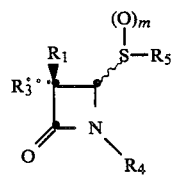

or

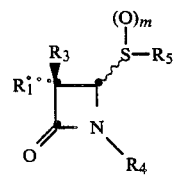

where $R_1$, $R_3$, $R_4$ and $R_5$ have the meaning given above, and m stands for 1 or 2, compounds of formulas

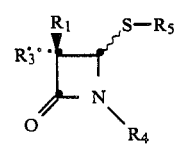

or

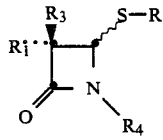

where $R_1$, $R_3$, $R_4$ and $R_5$ have the meaning given above, are oxidized, or (h) to prepare compounds of formula

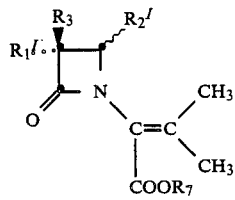

where $R_1^I$, $R_2$, $R_3$ and $R_7$ have the meaning given above, compounds of formula

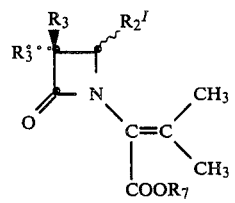

where $R_2^I$, $R_3$ and $R_7$ have the meaning given above, are reacted with the corresponding aldehyde and the hydroxy group is, if necessary, subsequently protected by a protecting group, and, if appropriate, a protecting group is introduced into compounds of formulas I and Ia where $R_4$ is hydrogen.

Process variant (a) can, for example, be carried out by dissolving a compound of formula III in a solvent that is inert in the reaction conditions, e.g. in an ether such as tetrahydrofuran or in a chlorinated hydrocarbon such as dichloromethane, and allowing it to react with a compound of formula IV, preferably at a temperature between low and ambient temperature, e.g. at around 0° C. Halogen can, for example, be used as the leaving group.

Process (b) can be carried out using halogenation methods known per se or known methods for introducing the acetate group. One example of such a halogenation method would be to react a compound of formula IIIa with a solution of the halogen concerned in a solvent that is inert under the reaction conditions, e.g. in a halogenated hydrocarbon (such as chlorine in arbon tetrachloride) at a low temperature, e.g. around 0° C. To introduce the acetate group a compound such as that of formula IIIa could be reacted in acetic acid with mercury(II)acetate at elevated temperature, e.g. around 100° C.

Process variant (c) of the invention can be carried out by treating a compound of formula If or Ig in a solvent that is inert under the reaction conditions, e.g. in a lower ketone such as acetone, with an oxidizing agent such as a mixture of $KMnO_4$ and $NaIO_4$, or reacting said compound with ozone, followed by methanol and a catalytic amount of a base such as triethylamine.

The fluorination according to process (d) can be carried out using known methods, for instance with a dialkylamino sulphur trifluoride such as diethylamino sulphur trifluoride, and preferably in a solvent that is insert in the reaction conditions, e.g. in a chlorinated hydrocarbon such as dichloromethane, and at a low temperature, e.g. around 0° C.

Processes (e) and (f) can be carried out by reacting, for example, a halogen compound of formulas In or Io in a solvent tht is insert in the reaction conditions such as tetrahydrofuran, dimethylformamide or dichloromethane, at temperatures from 0° to 60° C. with a corresponding anion or causing a compound of formula Ir or Is in aqueous or alcoholic systems to react with the corresponding anion at ambient temperature.

Oxidation of the sulphur as in process (g) can, for example, be carried out by dissolving a compound of formula Iv or Iw in a solvent that is inert in the reaction conditions, e.g. in a chlorinated hydrocarbon such as dichloromethane, and oxidizing said compound using known methods, e.g. with $H_2O_2$ and formic acid or acetic acid.

The protecting groups which are present can be split off using methods known per se. The compounds of formulas I and Ia can be isolated from the reaction mixture using known methods and purified if necessary.

The preparation and conversion of esters, protected forms and salt forms can likewise be performed using methods known per se.

The lower alkyl groups have 1 to 6 carbon atoms, particularly 1 to 4 and preferably 1 or 2. The alkenyl groups preferably have 2 to 4 carbon atoms, especially 2 or 3. n preferably stands for 0 or 2. Aryl stands preferably for phenyl, which can be optionally substituted.

The protecting groups used are those conventionally used in antibiotics chemistry for OH, $NH_2$ and COOH, for example p-nitrobenzyl, p-nitrobenzyloxycarbonyl, t-butyldimethylsilyl and trimethylsilyl.

Physiologically hydrolysable and compatible ester groups (also known as readily splitting ester groups) are those that can be hydrolyzed under physiological conditions and so give acids which in turn are physiologically compatible.

Examples of such esters are acetoxymethyl, 1-acetoxyethyl, 1-ethoxycarbonyloxyethyl, 5-indanyl and preferably pivaloyloxymethyl, hexanoyloxymethyl, phthalidyl, ethoxycarbonylmethoxymethyl or 3-ethoxycarbonyl-1-acetonyl.

It goes without saying that certain protecting groups can act as physiologically hydrolyzable and compatible ester groups and vice versa.

The compounds of formulas I and Ia are valuable intermediates for the manufacture of antibiotics of the carbapenem and penem class. In the latter the substituent $R_1$ may display $\alpha$ or $\beta$ configuration. The presence of an additional chirality centre in $R_1$ means that four isomers are possible, the preferred ones of these being those where for $\alpha$-constant $R_1$ the latter's additional chirality centre possesses the (R) configuration and for $\beta$-constant $R_1$ the (S) configuration. It is therefore of the greatest practical importance to have the best possible stereochemical control. In addition, the reaction in the case of substitution reactions on the hydroxy group in $R_1$ can alternatively be controlled so as to produce either inversion or retention. Furthermore, where $R_1$ is present as a steric arrangement this affects the configuration at $C_4$ of the azetidinone ring in $R_2$ substitution reactions. Conversely, where the configuration of $R_2$ is preset the reductive removal of $R_3$ can be so controlled that $R_1$ and $R_2$ can be in cis or trans arrangement with each other.

The compounds of formula Iy required as starting products for processes (h) can be obtained by allowing compounds of formula

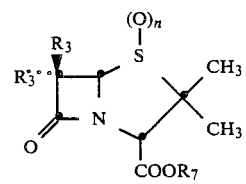

where $R_3$, $R_7$ and n have the meaning given above, to react with a compound of formula IV.

In the following Examples, which are intended to illustrate the present invention but in no way limit its scope, all temperatures are given in degrees Celsius.

EXAMPLE 1

2-[3α-Bromo-3β[1(R)-hydroxyethyl]-4(R)-methyl sulphonyl-2-oxazetidino-1-yl]-3-methylbut-2-enic acid methyl ester (Process a)

7.78 ml of 1,8-diazabicyclo[5.4.0]-undec-7-en are added to a glacial solution of 9.6 g 6α-bromo-6β-1(R)-hydroxyethylpenicillanic acid methyl ester-1,1-dioxide. After 20 minutes 18 ml $CH_3I$ are added. The reaction mixture is allowed to come to room temperature, stirred for a further two hours and then washed once with water, once with 0.1N HCl and once with saturated NaCl solution. After drying it over $MgSO_4$ the solution is evaporated and the residue crystallized from dichloromethane/heptane. NMR ($CDCl_3$): 1.60 (d, 3, J=6.5 Hz); 2.16 (s, 3); 2.30 (s, 3); 2.90 (s, 3); 3.76 (br, 1); 3.82 (s, 3); 4.68 (br q, 1, J=6.5 Hz); 5.46 (s, 1).

EXAMPLE 2

2-[3α-Bromo-3β-[1(S)-fluoroethyl]-4(R)-methylsulphonyl-2-oxoazetidino-1-yl]-3-methylbut-2-enic acid methyl ester (Process d)

A solution of 0.25 g 2-[3α-bromo-3β-[1(R)-hydroxyethyl]-4(R)-methylsulphonyl-2-oxoazetidino-1-yl]-3-methylbut-2-enic acid methyl ester in 5 ml of dry dichloromethane is added to a solution of 0.1 ml diethylaminosulphurtrifluoride and 0.125 g potassium fluoride in 5 ml of dry dichloromethane, the latter solution having been cooled to 0°. The mixture is allowed to come to room temperature, stirred for a further 30 minutes and then poured onto dichloromethane and saturated $NaHCO_3$ solution. The organic phase is dried over $MgSO_4$ and concentrated. The title compound is obtained by chromatography of the residue on silica gel (cyclohexane/ethyl acetate=1/1). NMR ($CDCl_3$): 1.60 (dd, 3, J=24.5 and 6 Hz); 2.10 (s, 3); 2.30 (s, 3); 3.10 (s, 3); 3.82 (s, 3); 5.38 (s, 1); 5.62 (dq, 1, J=45.5 and 6 Hz).

EXAMPLE 3

2-[3α-Bromo-3β-[1(R)-hydroxyethyl]-4(S)-methylthio-2-oxoazetidino-1-yl]-3-methylbut-2-enic acid methylester (A) and
2-[3α-bromo-3β-[1(R)-hydroxyethyl]-4(R)-methylthio-2-oxazetidino-1-yl]3-methylbut-2-enic acid methyl ester (B) (Process a)

6.16 ml of triethylamine and 20 mg dimethylaminopyridine are added to a solution, cooled to 0° and stirred, of 13.33 g 6α-bromo-6β-[1(R)-hydroxyethyl]penicillanic acid methyl ester in 150 ml of dry tetrahydrofuran, followed by the addition of 6.08 ml of chlorotrimethylsilane. The mixture is then stirred for 16 hours at room temperature. After removing the precipitate by filtration, the solution is added to a NaH suspension (1.5 g, 80%, prewashed with pentane). 25 ml of methyliodide are then added to this suspension and the resulting mixture is stirred at room temperature and in complete darkness for 3 days. A further 10 ml of methyliodide are then added and stirred again for 24 hours. The mixture is next diluted with ether, washed once each with 0.1N HCl and saturated NaCl solution and finally dried. Evaporation of the solvent produces an oil, which after chromatography with silic gel (ethyl acetate/cyclohexane=1/1) gives 3.5 g of Product (A) and 0.15 g of Product (B), together with 8.8 g of the silylized mixture of (A) and (B). This silylized mixture is dissolved in 70 ml of a mixture of methanol/water (9/1) and 8.75 ml of concentrated hydrochloric acid are added to this solution. After 2 hours water is added to the reaction mixture and the methanol is evaporated in vacuo. The residue is absorbed in ethyl acetate, washed once each with water and saturated NaCl solution, the organic phase dried over MgSO4 and concentrated. Chromatography of the residue with silica gel gives a further 2.57 g of Product (A) and 4.65 g of Product (B).

(A): NMR (CDCl3): 1.45 (d, 3, J=6 Hz); 2.06 (s, 3); 2.15 (s, 3); 2.30 (s, 3); 2.53 (d, 1, J=4.5 Hz); 3.80 (s, 3); 4.24 (dq, 1, J=6 and 4.5 Hz); 5.26 (s, 1).

(B): NMR (CDCl3): 1.58 (d, 3, J=6 Hz); 2.04 (s, 3); 2.23 (s, 3); 2.30 (s, 3); 2.86 (s, 1, J=4.5 Hz); 3.81 (s, 3); 4.26 (dq, 1, J=6 and 4.5 Hz); 5.24 (s, 1).

EXAMPLE 4

2-[3α-Bromo-3β-[1(R)-hydroxyethyl]-4(S)-methylsulphonyl-2-oxoazetidino-1-yl]-3-methylbut-2-enic acid methyl ester (Process g)

0.5 g 2-[3α-bromo-3β-[1(R)-hydroxyethyl]-4(S)-methylthio-2-oxoazetidino-1-yl]-3-methylbut-2-enic acid methyl ester is dissolved in 5 ml of dichloromethane, and 1.6 ml hydrogen peroxide (30%) and 2.6 ml formic acid are then added. The solution is stirred for 72 hours at room temperature. The reaction mixture is then diluted with dichloromethane, washed once each with water, 5% NaHCO3 solution, and saturated NaCl solution, dried over MgSO4 and concentrated in a rotary evaporator. The residue is crystallized from dichloromethane/heptane. NMR (CDCl3): 1.50 (d, 3, J=6 Hz); 2.15 (s, 3); 2.28 (s, 3); 2.56 (d, 1, J=4.5 Hz); 3.00 (s, 3); 3.84 (s, 3); 4.32 (dq, 1, J=6 and 4.5 Hz); 5.32 (s, 1).

EXAMPLE 5

2-[3α-Bromo-3β-[1(R)-fluoroethyl]-4(S)-methylsulphonyl-2-oxoazetidino-1-yl]-3-methylbut-2-enic acid methyl ester (Process d)

To a solution, cooled to −78°, of 0.5 ml diethylaminosulphurtrifluoride and 0.5 g potassium fluoride in 10 ml of dry dichloromethane is added a solution of 0.43 g 2-[3α-bromo-3β-[1(R)-hydroxyethyl]-4(S)-methylsulphonyl-2-oxoazetidino-1-yl]-3-methylbut-2-enic acid methyl ester in 10 ml of dry dichloromethane. The mixture is allowed to come to room temperature, stirred for a further hour and then poured onto dichloromethane and saturated NaHCO3 solution. The organic phase is dried over MgSO4 and concentrated. The title compound is obtained by chromatography of the residue on silica gel (cyclohexane/ethyl acetate=1/1).

NMR (CDCl3): 1.70 (dd, 3, J=24 and 6.5 Hz); 2.13 (s, 3); 2.28 (s, 3); 2.98 (s, 3); 3.82 (s, 3); 5.09 (dq, 1, J=46,5 u. 6,5 1 Hz); 5.41 (s, 1).

EXAMPLE 6

2-[4(S)-Acetoxy-3α-bromo-3β-[1(R)-hydroxyethyl]-2-oxoazetidino-1-yl]-3-methylbut-2-enic acid methyl ester (A) and
2-[4(R)-Acetoxy-3α-bromo-3β-[1(R)-hydroxyethyl]-2-oxoazetidino-1-yl]-3-methylbut-2-enic acid methyl ester (B) (Process b)

2 g mercury(II)acetate are added to a solution of 2.12 g 6α-bromo-6β-[1(R)-hydroxyethyl]-penicillanic acid methyl ester in 30 ml of acetic acid and stirred for 5 hours at 100°. After cooling down it is filtered, the filtrate dried and then removed three times with toluene. Next the residue is absorbed in ethyl acetate and filtered once again to remove insoluble matter. The filtrate is extracted three times with water, dried over MgSO4 and concentrated. The residue is chromatographed on silica gel (ethyl acetate/cyclohexane=1/1). The title compounds are thus obtained.

(A): NMR (CDCl3): 1.50 (d, 3, J=7 Hz); 2.04 (s, 3); 2.17 (s, 3); 2.28 (s, 3); 2.56 (d, 1, J=7 Hz); 3.80 (s, 3); 4.26 (q, 1, J=7 Hz); 6.18 (s, 1).

(B): NMR (CDCl3): 1.44 (d, 3, J=7 Hz); 2.01 (s, 3); 2.14 (s, 3); 2.26 (s, 3); 2.54 (d, 1, J=7 Hz); 3.80 (s, 3); 4.28 (q, 1, J=7 Hz); 6.42 (s, 1).

EXAMPLE 7

2-[3α-Bromo-3β[1(R)-tert.butyldimethylsilyloxyethyl]-4(R)-methylsulphonyl-2-oxoazetidino-1-yl]-3-methylbut-2-enic acid methyl ester (Introduction of Protecting Group)

40 mg dimethylaminopyridine and 0.39 g tert.butyldimethylsilylchloride are added to a solution, cooled to 0°, of 0.25 g 2-[3α-bromo-3β[1(R)-hydroxyethyl]-4(R)-methylsulphonyl-2-oxoazetidino-1-yl]-3-methylbut-2-enic acid methyl ester in 1.5 ml dimethylformamide. The solution is allowed to come to room temperature, stirred for a further 16 hours and then diluted with ethyl acetate and water. The organic layer is washed once with 0.1N HCl, several times with H2O and after drying over MgSO4 is concentrated. The resulting residue is purified by passing it through a small silica gel column (cyclohexane/ethyl acetate=3/1). NMR (CDCl3): 0.08 (s, 3); 0.09 (s, 3); 0.90 (s, 9); 1.49 (d, 3, J=6 Hz); 2.12 (s, 3); 2.28 (s, 3); 2.82 (s, 3); 3.80 (s, 3); 4.70 (q, 1, J=6 Hz); 5.28 (s, 1).

EXAMPLE 8

3α-Bromo-3β-[1(R)-tert.butyldimethylsilyloxyethyl]-4(R)-methylsulphonyl-2-oxoazetidine (Process c)

To a solution of 150 mg KMnO$_4$ and 700 mg NaJO$_4$ in 6 ml of phosphate buffer (pH 7.1) is added a solution of 0.6 g 2-[3α-bromo-3β-[1(R)-tert.butyldimethylsilyloxyethyl]-4(R)-methylsulphonyl-2-oxoazetidino-1-yl]-3-methylbut-2-enic acid methyl ester in 6 ml of acetone. The reaction mixture is stirred for 16 hours at room temperature. After the inorganic material has been filtered and the filtrate washed with acetone, the solutions are concentrated in a rotary evaporator. The residue is absorbed in ethyl acetate, washed with water and after drying over MgSO$_4$ is concentrated. The title compound is obtained by direct crystallization of the residue (diisopropylether/heptane). Fp: 139°–141°.

NMR (CDCl$_3$): 0.09 (s, 6); 0.90 (s, 9); 1.44 (d, 3, J=6 Hz); 2.99 (s, 3); 4.68 (q, 1, J=6 Hz); 4.88 (s, 1); 7.44 (br, 1).

EXAMPLE 9

3α-Bromo-3β-[1(R)-hydroxyethyl]-4(R)-methylsulphonyl-2-oxoazetidine (Process c)

The procedure is the same as described in Example 8.
NMR (CDCl$_3$): 1.50 (d, 3, J=6 Hz); 3.10 (s, 3); 4.04 (d, 1, J=4.5 Hz); 4.63 (dq, 1, J=6 and 4.5 Hz); 4.98 (s, 1); 9.48 (br, 1).

EXAMPLE 10

2-[3β-Bromo-3α-[1(S)-hydroxyethyl]-4(R)-methylsulphonyl-2-oxoazetidino-1-yl]-3-methylbut-2-enic acid methyl ester (Process h)

0.88 ml of a 3M solution of methylmagnesium bromide in ether is added to a solution, cooled to −78°, of 2.2 g 2-[3,3-dibromo-4(R)-methylsulphonyl-2-oxoazetidino-1-yl]-3-methylbut-2-enic acid methyl ester in 30 ml of dry tetrahydrofuran. After 30 minutes 0.73 ml freshly distilled acetaldehyde is added, the reaction mixture is allowed to come to room temperature, and stirring is continued for two more hours. The mixture is brought to pH 6 with saturated NH$_4$Cl solution and poured onto ethyl acetate. The organic layer is washed with water and saturated NaCl solution and after drying over MgSO$_4$ is concentrated. The residue is chromatographed on silica gel (cyclohexane/ethyl acetate=½). Fp: 142°14 146°.

EXAMPLE 11

2-[3β-Bromo-3α-[1(S)-tert.butyldimethylsilyloxyethyl]-4(R)-methylsulphonyl-2-oxoazetidino-1-yl]-3-methylbut-2-enic acid methyl ester:

0.8 g dimethylaminopyridine and 2 g tert.butyldimethylsilylchloride are added to a solution, cooled to 0°, of 1.26 g 2-[3β-bromo-3α-[1(S)-hydroxyethyl]-4(R)-methylsulphonyl-2-oxoazetidino-1-yl]-3-methylbut-2-enic acid methyl ester in 12 ml of dimethylformamide. The solution is allowed to come to room temperature, stirred for a further 16 hours and then diluted with ethyl acetate and water. The organic layer is washed once with 0.1N HCl, several times with water, and concentrated after being dried over MgSO$_4$. The resulting residue is purified by passing it through a small silica gel column (cyclohexane/ethyl acetate=3/1). An oily product is obtained.

NMR (CDCl$_3$): 0.14 (s, 3); 0.16 (s, 3); 0.92 (s, 9); 1.44 (d, 3, J=6.5 Hz); 2.12 (s, 3); 2.26 (s, 3); 3.02 (s, 3); 3.82 (s, 3); 4.38 (q, 1, J=6.5 Hz); 5.35 (s, 1).

EXAMPLE 12

3β-Bromo-3α-[1(S)-tert.butyldimethylsilyloxyethyl]-4(R)-methylsulphonyl-2-oxoazetidine (Process c)

The procedure is the same as described in Example 8.
NMR (CDCl$_3$): 0.13 (s, 3); 0.15 (s, 3); 0.90 (s, 9); 1.46 (d, 3, J=6.5 Hz); 3.13 (s, 3); 4.29 (q, 1, J=6.5 hz); 4.78 (s, 1); 7.02 (br, 1).

EXAMPLE 13

2-[3β-Bromo-3α-[1(S)-fluoroethyl]-4(R)-methylsulphonyl-2-oxoazetidino-1-yl]-3-methylbut-2-enic acid methyl ester To a solution, cooled to −78°, of 4.8 ml diethylaminosulphurtrifluoride and 5.9 g potassium fluoride in 100 ml of dry dichloromethane is added a solution of 5 g 2-[3β-bromo-3α-[1(S)-hydroxyethyl]-4(R)-methylsulphonyl-2-oxoazetidino-1-yl]-3-methylbut-2-enic acid methyl ester in 100 ml of dry dichloromethane. The mixture is allowed to come to room temperature, stirred for another hour and then poured onto dichloromethane and saturated NaHCO$_3$ solution. The organic phase is dried over MgSO$_4$ and concentrated. Chromatography of the residue on silica gel (cyclohexane/ethyl acetate=1/1) gives the title compound. Fp: 147°–149°. NMR (CDCl$_3$): 1.71 (dd, 3, J=24 and 6.5 Hz); 2.14 (s, 3); 2.30 (s, 3); 3.00 (s, 3); 3.83 (s, 3); 5.10 (dq, 1, J=41.5 and 6.5 Hz); 5.42 (s, 1).

These compounds of formulas I and Ia obtained in this manner can, for example, be reacted further as follows:

(A)

2-[3(R)-[1(R)-Fluoroethyl]-4(S)-methylsulphonyl-2-oxoazetidino-1-yl]-3-methylbut-2-enic acid methyl ester 0.1 ml n-tributyl stannic hydride is added to a solution of 100 mg 2-[3α-bromo-3β-[1(R)-fluoroethyl]-4(S)-methylsulphonyl-2-oxoazetidino-1-yl]-3-methylbut-2-enic acid methyl ester (compound from Example 5) and 15 mg α,α′-azoisobutyronitrile in 3 ml of toluene. The mixture is heated for one hour to 80°; the mixture is then allowed to come to room temperature and poured onto ether and saturated potassium fluoride solution. The organic phase is washed with saturated NaCl solution, dried over MgSO$_4$ and concentrated. Chromatography of the residue on silica gel (dichloromethane/ether=10/1) gives the title compound.

NMR (CDCl$_3$): 1.59 (dd, 3, J=2.5 and 6.5 Hz); 2.12 (s, 3); 2.27 (s, 3); 3.02 (s, 3); 3.80 (s, 3); 3.84 (dt, 1, J=10.5 and 5 Hz); 5.16 (d, 1, J=5 Hz); 5.63 (ddq, 1, J=48.5, 10.5 and 6.5 Hz).

(B)

2-[3(S)-[1(R)-tert.butyldimethylsilyloxyethyl]-4(R)-methylsulphonyl-2-oxoazetidino-1-yl]-3-methylbut-2-enic acid methyl ester A suspension of 2-[3α-bromo-3β[1(R)-tert.butyldimethylsilyloxyethyl]-4(R)-methylsulphonyl-2-oxoazetidino-1-yl]-3-methylbut-2-enic acid methyl ester (compound from Example 7) and 20 mg 10% Pd/C in 20 ml of methanol and 0.1 ml 1,8-diazabicyclo-[5.4.0]-undec-7-en are hydrated for one hour at 20° and 3 bars hydrogen pressure (Parr Shaker). After the catalyst has been filtered and the filtrate washed with methanol, the two solutions are concentrated in a rotary evaporator. The residue is absorbed in ethyl acetate, washed once with 0.1N HCl and once with saturated NaCl solution. The solution is dried over MgSO4 and concentrated by evaporation. The residue is passed through a small silica gel column (dichloromethane/ether=20/1).

NMR (CDCl3): 0.04 (s, 3); 0.08 (s, 3); 0.84 (s, 9); 1.28 (d, 3, J=6.5 Hz); 2.04 (s, 3); 2.22 (s, 3); 2.84 (s, 3); 3.60 (dd, 1, J=4.5 and 2.5 Hz); 3.78 (s, 3); 4.35 (dq, 1, J=6.5 and 4.5 Hz); 5.26 (d, 1, J=2.5 Hz).

(C)
3(S)-[1(R)-tert.butyldimethylsilyloxyethyl]-4(R)-methyl-sulphonyl-2-oxoazetidine To a solution of 20 mg KMnO4 and 0.1 g NaJO4 in 5 ml of phosphate buffer (pH 7.1) is added a solution of 80 mg 2-[3(S)-[1(R)-tert.butyldimethylsilyloxyethyl]-4(R)-methylsulphonyl-2-oxoazetidino-1-yl]-3-methylbut-2-enic acid methyl ester (compound B)) in 3 ml of acetone. The reaction mixture is stirred for one hour at room temperature. After filtering to remove inorganic material and washing the residue with acetone, the solutions are concentrated in a rotary evaporator. The residue is absorbed in ethyl acetate, washed with water and after being dried over MgSO4 is concentrated. NMR (CDCl3): 0.10 (s, 3); 0.12 (s, 3); 0.89 (s, 9); 1.30 (d, 3, J=6.5 Hz); 2.98 (s, 3); 3.58 (ddd, 1, J=2.5, 2 and 0.5 Hz); 4.36 (dq, 1, J=6.5 and 2.5 Hz); 4.76 (d, 1, J=2 Hz); 6.70 (br, 1).

The 2-[3,3-dibromo-4(R)-methylsulphonyl-2-oxoazetidino-1-yl]-3-methylbut-2-enic acid methyl ester required as a starting product can be obtained in the following manner:

(a) 6,6-Dibromopenicillanic acid methyl ester 1,1 dioxide 100 g 6,6-dibromopenicillanic acid methyl ester are dissolved in 900 ml of glacial acetic acid (80%). 100 g potassium permanganate are added and stirred for two hours at room temperature. 60 ml of 30% H2O2 are added to this suspension until it becomes almost colourless, the reaction mixture is then brought to pH 6.5 with NaHCO3 and extracted several times with dichloromethane. The organic phase is dried over MgSO4 and then concentrated. The residue is absorbed several times in toluene and concentrated in a rotary evaporator and then recrystallized from dichloromethane/ether. Fp. 184°-189°. NMR (CDCl3): 1.42 (s, 3); 1.62 (s, 3); 3.87 (s, 3); 4.54 (s, 1); 5.05 (s, 1).

(b)
2-[3,3-Dibromo-4(R)-methylsulphonyl-2-oxoazetidino-1-yl]-3-methylbut-2-enic acid methyl ester 12 ml 1,5-diazabicyclo[4.3.0]non-5-en are added to a glacial solution of 30 g 6,6-dibromopenicillanic acid methyl ester 1,1 dioxide. After 20 minutes 45 ml of CH3J are added. The reaction mixture is allowed to come to room temperature, stirred for a further two hours and then washed once with water, once with 0.1N HCl and once with saturated NaCl solution. After drying it over MgSO4 the solution is concentrated by evaporation, and the residue is crystallized from dichloromethane/diisopropylether. Fp: 161°-164°.

NMR (CDCl3): 2.16 (s, 3); 2.32 (s, 3); 3.08 (s, 3); 3.84 (s, 3); 5.57 (s, 1).

We claim:
1. New 2-oxoazetidines having the formulas

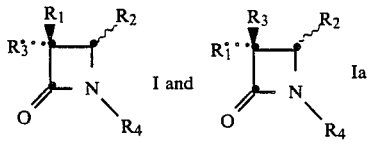

wherein
$R_1$ is lower fluoroalkyl, lower hydroxyalkyl or protected lower hydroxyalkyl;
$R_2$ is chlorine, bromine, iodine, fluorine,

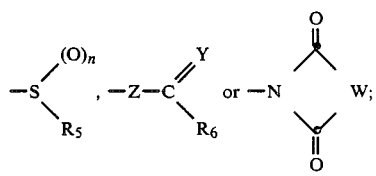

$R_3$ is bromine, chlorine, iodine, SeC6H5 or SC6H5;
$R_4$ is H or

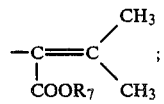

$R_5$ is lower alkyl, lower alkenyl, benzyl, phenyl or —CH2COX $R_6$ is lower alkyl, lower alkoxy, lower alkylthio, lower dialkylamino, aryl, aryloxy, or arylthio;
$R_7$ is lower alkyl, benzyl, or benzhydryl;
Z is O, NH or S;
Y is O, N or S;
X is lower alkyl, lower alkoxy or amino;
W is —CH2CH2, —CH=CH— or C6H4; and
n is 1 or 2.

2. The 2-oxoazetidines of claim 1 wherein said formula is Ia and $R_2$ is

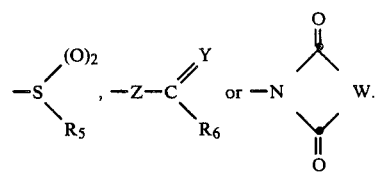

3. New 2-oxoazetidines having the formulas

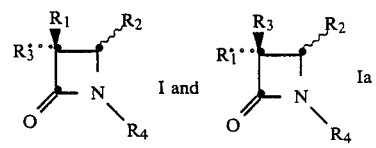

wherein
$R_1$ is lower fluoroalkyl;
$R_2$ is chlorine, bromine, iodine, fluorine,

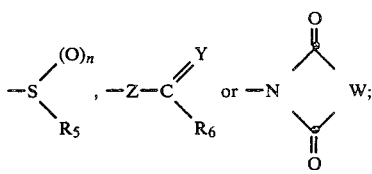

R₃ is bromine, chlorine, iodine, SeC₆H₅ or SC₆H₅;
R₄ is H or

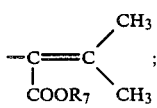

R₅ is lower alkyl, lower alkenyl, benzyl, phenyl or —CH₂COX

R₆ is lower alkyl, lower alkoxy, lower alkylthio, lower dialkylamino, aryl, aryloxy, or arylthio;
R₇ is lower alkyl, benzyl, or benzhydryl;
Z is O, NH or S;
Y is O, N or S;
X is lower alkyl, lower alkoxy or amino;
W is —CH₂CH₂, —CH=CH— or C₆H₄; and
n is 0, 1 or 2.

4. 2-oxoazetidines having the formulas

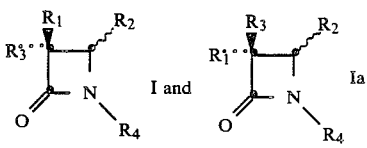

wherein
R₁ is lower fluoroalkyl, lower hydroxyalkyl or protected lower hydroxyalkyl;
R₂ is chlorine, bromine, iodine, fluorine,

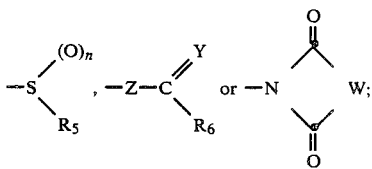

R₃ is SeC₆H₅ or SC₆H₅;
R₄ is H or

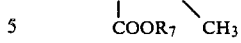

R₅ is lower alkyl, lower alkenyl, benzyl, phenyl or —CH₂COX;
R₆ is lower alkyl, lower alkoxy, lower alkylthio, lower dialkylamino, aryl, aryloxy, or arylthio;
R₇ is lower alkyl, benzyl, or benzhydryl;
Z is O, NH or S;
Y is O, N or S;
X is lower alkyl, lower alkoxy or amino;
W is —CH₂CH₂, —CH=CH— or C₆H₄; and
n is 0, 1 or 2.

5. New 2-oxoazetidines having the formulas

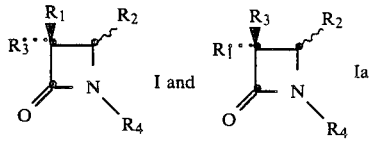

wherein
R₁ is lower fluoroalkyl, lower hydroxyalkyl or protected lower hydroxyalkyl;
R₂ is chlorine, bromine, iodine, fluorine,

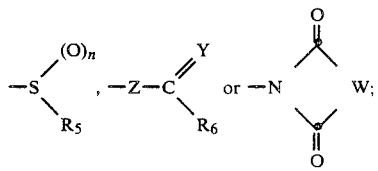

R₃ is bromine, chlorine, iodine, SeC₆H₅ or SC₆H₅;
R₄ is H or

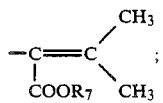

R₅ is benzyl, phenyl or —CH₂COX;
R₆ is lower alkyl, lower alkoxy, lower alkylthio, lower dialkylamino, aryl, aryloxy, or arylthio;
R₇ is lower alkyl, benzyl, or benzhydryl;
Z is O, NH or S;
Y is O, N or S;
X is lower alkyl, lower alkoxy or amino;
W is —CH₂CH₂, —CH=CH— or C₆H₄; and
n is 0, 1 or 2.

* * * * *